US012589020B2

(12) United States Patent
      Barng

(10) Patent No.: US 12,589,020 B2
(45) Date of Patent: Mar. 31, 2026

(54) CURETTE TOOL AND NAIL CARE METHOD USING SAME

(71) Applicant: BARNG KEE JUNG CORP., Pyeongtaek-si (KR)

(72) Inventor: Keejung Barng, Pyeongtaek-si (KR)

(73) Assignee: BARNG KEE JUNG CORP., Pyeongtaek-si (KR)

( * ) Notice: Subject to any disclaimer, the term of this patent is extended or adjusted under 35 U.S.C. 154(b) by 175 days.

(21) Appl. No.: 18/569,126

(22) PCT Filed: Jun. 9, 2023

(86) PCT No.: PCT/KR2023/007921
      § 371 (c)(1),
      (2) Date: Dec. 11, 2023

(87) PCT Pub. No.: WO2024/232467
      PCT Pub. Date: Nov. 14, 2024

(65) Prior Publication Data
      US 2025/0082491 A1      Mar. 13, 2025

(30) Foreign Application Priority Data
      May 8, 2023      (KR) ........................ 10-2023-0058952

(51) Int. Cl.
      *A61F 5/11*      (2006.01)
(52) U.S. Cl.
      CPC ..................................... *A61F 5/11* (2013.01)
(58) Field of Classification Search
      CPC ........ A45D 29/06; A45D 29/16; A45D 29/17; A45D 31/00
      See application file for complete search history.

(56) References Cited

U.S. PATENT DOCUMENTS 2,479,514 A * 8/1949 Rucker .................. A61B 17/54
                                                                    132/75.6
2,801,640 A * 8/1957 Steele .................... A45D 29/06
                                                                    7/162

(Continued)

FOREIGN PATENT DOCUMENTS

JP       2020-198954 A      12/2020
KR   10-2014-0078709 A       6/2014

(Continued)

OTHER PUBLICATIONS

Korean Office Action for related KR Application No. 10-2023-0058952 mailed Sep. 18, 2023 from Korean Intellectual Property Office.

(Continued)

*Primary Examiner* — Rachel R Steitz
(74) *Attorney, Agent, or Firm* — Paratus Law Group, PLLC

(57) ABSTRACT

A curette tool includes: a first curette part which has an insert plate and a blade extending upward perpendicularly along the outer circumference on one side of the insert plate; a second curette part which is formed symmetrically to the first curette part; and a grip part which is formed in a bar shape with the first and second curette parts respectively installed at each end thereof. Any one of the first and second curette parts is inserted into the side wall of a target nail, and the blade pushes outward the skin tissue adjacent to the side wall to secure a nail grooming space.

2 Claims, 6 Drawing Sheets

(56)                  References Cited

U.S. PATENT DOCUMENTS

2008/0078085  A1*    4/2008   Wittke-Kothe  ........  A45D 29/16
                                                          30/26
2018/0310687  A1     11/2018  Gomes

FOREIGN PATENT DOCUMENTS

KR      10-2019-0135097  A      12/2019
KR      10-2022-0166152  A      12/2022

OTHER PUBLICATIONS

Korean Notice of Allowance for related KR Application No. 10-2023-0058952 mailed Feb. 26, 2024 from Korean Intellectual Property Office.

* cited by examiner

S100

CURETTE TOOL AND NAIL CARE METHOD USING SAME

CROSS-REFERENCE TO PRIOR APPLICATIONS

This Application is a National Stage Patent Application of PCT International Application No. PCT/KR2023/007921 (filed on Jun. 9, 2023), which claims priority to Korean Patent Application No. 10-2023-0058952 (filed on May 8, 2023), which are all hereby incorporated by reference in their entirety.

BACKGROUND

The present invention relates to a curette tool for forming a nail grooming space for the nail care of fingernails and toenails, and a nail care method using the same.

Deformed fingernails or toenails are one of the common nail disorders with over 200,000 patients occurring annually, and means a disease causing pain by nail ends digging into the skin due to the deformation of the nails. The nail disorder may be induced by situations that the nails continuously press against the outside of the skin due to various environmental factors. The prevalence rate of such nail deformation is high among the elderly, and with the growing aging population, there is a demand for treatment methods.

The most representative symptoms include warmth, pain and swelling at the site of an outbreak, and the most commonly affects the big toe among the five toes, especially on the right foot. Initially, the outside or inside of the big toe may become slightly red and swollen with mild pain, but as friction continues and worsens, the swelling increases, a sore oozes, and inflammation occurs with the proliferation of vascular and fibrous tissue masses, worse as the area around the nail begins to so pain grows deteriorate.

Moreover, nail disorders can occur due to various causes, such as deeply cutting deformed toenails, nail deformation by neglecting toenail fungus, wearing tight shoes for long periods, or natural changes like increased curvature of the toenail due to obesity or aging. Such patients need to refrain from all actions that apply pressure to the foot, soak their toes in clean physiological saline for disinfection, and pay attention to regular nail care.

However, despite such careful management, since the nail disorders are prone to recurrence if nail care is neglected, the nail disorders require meticulous management and caution. Correction of ingrown toenails is the most common and crucial treatment method for ingrown toenail diseases, and Korean Patent Publication No. 10-2022-0166152 discloses "Nail Correction Device". Various devices have been developed and used to correct and while unfolding deformed toenails.

However, since the care of everyday nail management is as important as the correction of ingrown toenail diseases, there is a need for nail care tools which can help care for ingrown toenails without using correction devices. As described above, continuous home care and professional management of deformed toenails are necessary, but it is difficult to perform self-care due to aging. Therefore, tools which are easy for maintaining and managing the shape of the nails without discomfort in daily life are in demand.

SUMMARY

Accordingly, the present invention has been made in view of the above-mentioned problems occurring in the related art, and it is an objective of the present invention to provide a curette tool, which can secure a nail grooming space by making a blade of the curette tool contact with the surface of the nail and pushing towards the skin tissues adjacent to side wall, and minimize skin irritation by selecting and using a suitable curette part according to the length and deformation degree of the side wall of a target nail, thereby enabling the separation of the cell membrane and foreign materials attached to the side wall of the nail. The technical objective specified above is not limited thereto, and other technical objectives may be derived from the following description.

To accomplish the above-mentioned objects, according to the present invention, there is provided a curette tool including: a first curette part which has an insert plate and a blade extending upward perpendicularly along the outer circumference on one side of the insert plate; a second curette part which is formed symmetrically to the first curette part; and a grip part which is formed in a bar shape with the first and second curette parts respectively installed at each end thereof, wherein any one of the first and second curette parts is inserted into the side wall of a target nail, and the blade pushes outward the skin tissue adjacent to the side wall to secure a nail grooming space.

Moreover, the insert plates of the first and second curette parts are formed symmetrically based on the central axis of the grip part in a streamlined shape.

Furthermore, each of the blades of the first and second curette parts includes a support wing formed along one side surface of the insert plate, and a guide wing extending from the support wing and protruding from the insert plate.

Additionally, the first and second curette parts are designed such that the insert plate has a uniform width in the longitudinal direction and is bent at a predetermined angle, and the blade includes a support wing formed along one side surface of the insert plate, and a guide wing extending from the support wing and protruding from the insert plate.

In another aspect of the present invention, provided is a nail care method including: a preparation step of preparing a curette tool; a space creation step in which the insert plate of the curette tool is inserted into the side wall of the target nail and the blade pushes outward the skin tissue adjacent to the side wall to secure a nail grooming space; a shape formation step of trimming the shape of the target nail and applying gel to form the shape of an artificial nail; a gel fixation step of curing and fixing the shape of the artificial nail with ultraviolet light; a curette removal step of removing the curette tool inserted into the side wall of the nail subject.

In addition, the preparation step includes: a cuticle removal step of removing cuticles or foreign substances from the nail subject; a pretreatment step of polishing the surface of the nail subject by sections of the target nail by using a surface polishing tool, and then, applying acrylic and curing for a predetermined period of time; a curette selection step of selecting the curette tool according to the length and deformed shape of the side wall of the target nail.

According to an embodiment of the present invention having the configuration as above, the curette tool and the nail care method using the same have the following advantages.

The curette tool can secure a nail grooming space by making a blade of the curette tool contact with the surface of the nail and pushing towards the skin tissue adjacent to the side wall, and minimize skin irritation by selecting and using a suitable curette part according to the length and deformation degree of the side wall of a target nail, thereby enabling the separation of the cell membrane and foreign materials attached to the side wall of the nail.

Furthermore, the curette tool can be easily used by unskilled persons, and since only one curette tool is required, it is not necessary to prepare many tools, thereby shortening the time and process of artificial nail operations.

In addition, the curette tool and the nail care method can minimize the skin irritation that may occur during the process of separating the cell membrane and foreign substances, thus allowing the cuticle to be cleanly separated from the surface of each fingernail or toenail. Moreover, the curette tool and the nail care method can reconstruct the skin deformed by ingrown nails, as well as the side walls of deformed nails.

Additionally, the curette tool and the nail care method can prevent bleeding since pushing and digging into the inside of the cuticle without irritating the adjacent skin tissue when rotating after the outermost point of the insert plate of the curette tool is fixed to the side wall.

In addition, the curette tool can be custom-selected according to the length and deformation shape of the side wall of a target nail, thereby allowing easy management and increased work efficiency. Moreover, A tool suitable for the shape of the target nail, thereby preventing injury to the user due to excessive insertion.

DETAILED DESCRIPTION

Figure 1A:
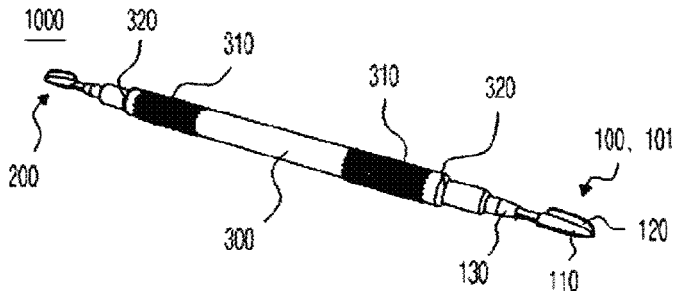
FIGS. 1A-1D are perspective views of curette tools according to embodiments of the present invention.

Hereinafter, the embodiment of the present invention will be described in detail with reference to the accompanying drawings so that it can be easily realized by a person with ordinary skill in the art to which the present invention pertains. The present invention can be realized in various different forms and is not limited to the structures or methods described herein.

In addition, with respect to the directions of the curette tool and the nail care method of the present invention, based on the curette part illustrated in FIGS. 3A-3D, the left direction is defined as 'one side,' the right direction as 'the other side,' the direction toward the ground as 'inward,' and the opposite direction as 'outward.' The front in the drawings is referred to as 'upward direction,' and the rear as 'downward direction.' The above definition is for clarity of understanding the invention and does not limit the definition of directions which can vary depending on where they are based.

Figure 1B:
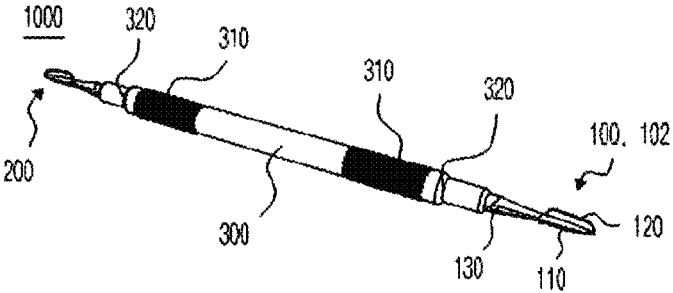
Figure 1C:
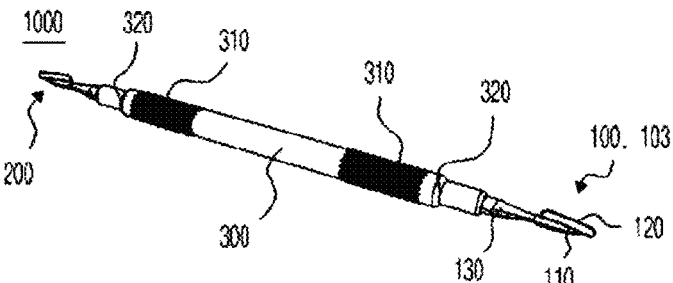
Figure 1D:
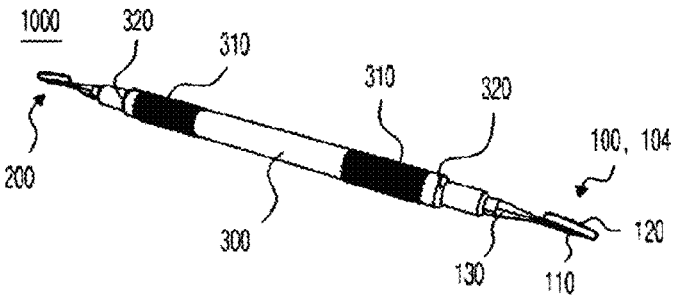
Figure 2A:
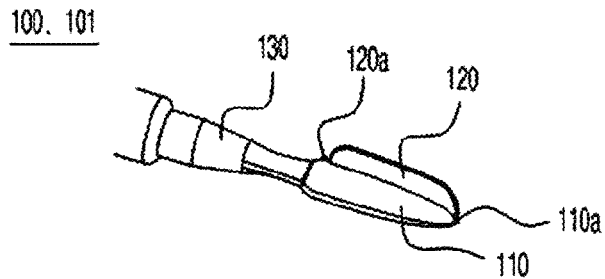
FIGS. 2A-2D are partially enlarged views of the curette tools according to embodiments of the present invention.
Figure 2B:
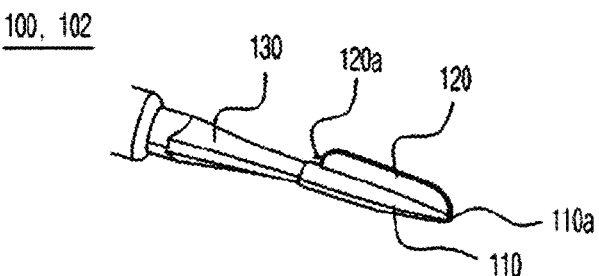
Figure 2C:
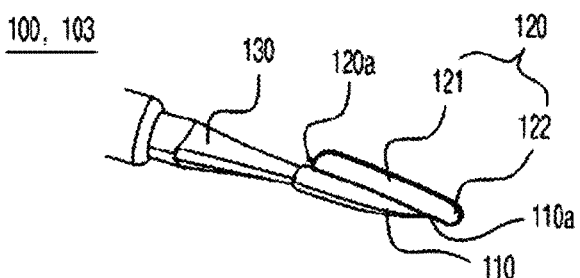
Figure 2D:
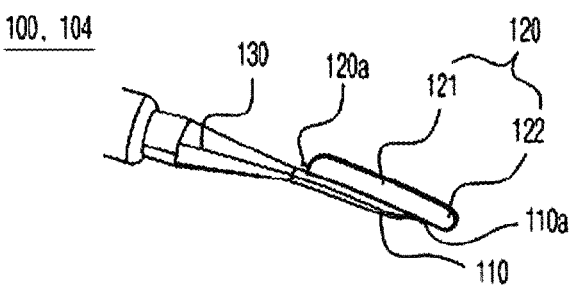
Figure 3A:
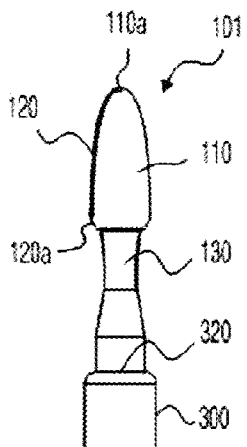
FIGS. 3A-3D are front views of the curette tools according to embodiments of the present invention.
Figure 3B:
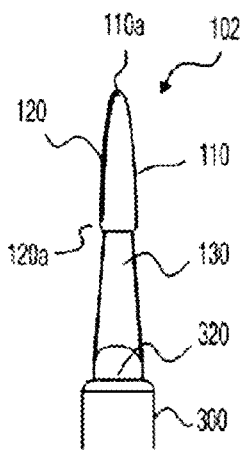
Figure 3C:
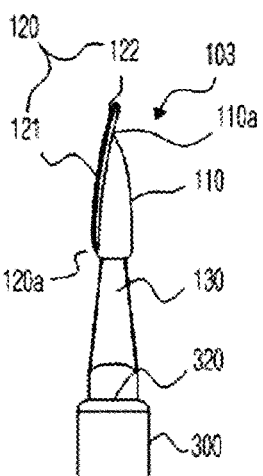
Figure 3D:
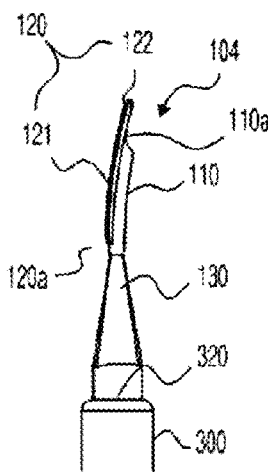
Figure 4A:
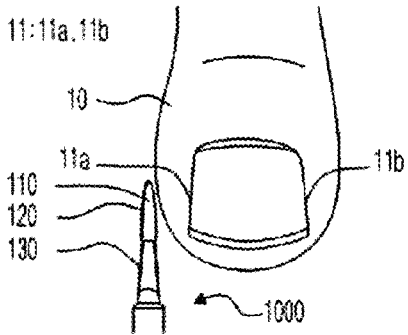
FIGS. 4A-4C are exemplary views illustrating used states of the curette tool according to an embodiment of the present invention.
Figure 4B:
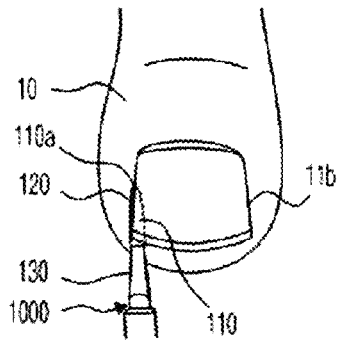
Figure 4C:
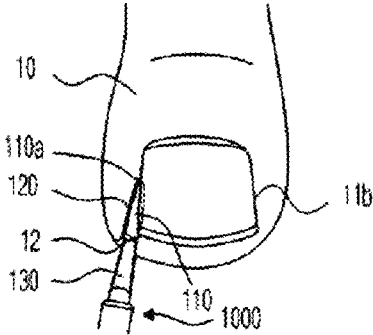

FIG. 1A is a perspective view of a modified expansion-type curette tool according to an embodiment of the present invention, and FIG. 1B is a perspective view of a modified reduction-type curette tool according to an embodiment of the present invention. Furthermore, FIG. 1C is a perspective view of a general toenail-type curette tool according to an embodiment of the present invention, and FIG. 1D is a perspective view of a general fingernail-type curette tool according to an embodiment of the present invention. FIGS. 2A-2D are partial enlarged views of FIGS. 1A-1D.

FIGS. 3A-3D are front views of the curette parts of FIGS. 1A-1D, and FIGS. 4A-4C are exemplary views illustrating used states of the curette tool according to an embodiment of the present invention.

Referring to FIGS. 1A-1D, 2A-2D, 3A-3D, and 4A-4C, the curette tool 1000 of the present invention is a tool for securing a nail grooming space by making the blade 120 contact with the surface of a fingernail or toenail and pushing in the direction of the skin tissue adjacent to side wall 11 while inserted into the side wall 11 of a target nail 10. The curette tool 1000 secures a nail grooming space 12 to enable reconstruction of the skin deformed by ingrown nails and the side wall 11 of the fingernail or the toenail, and facilitates the formation or grooming of an artificial nail shape by a unskilled person. Here, the side wall 11 of the target nail 10 refers to both sides of a fingernail or toenail.

Specifically, the curette tool 1000 allows for the securing of the nail grooming space 12 by pushing out the skin tissue adjacent to the side wall 11 using the blade 120 after one of curette parts is inserted into the side wall 11 of the target nail 10. Such a curette tool 1000 can include a first curette part 100 which is inserted into a first side wall 11a of the target nail 10 to push the adjacent skin tissue, a second curette part 200 which is inserted into a second side wall 11b of the target nail 10 to push the adjacent skin tissue, and a grip part 300 which is formed to be held by a user's hand to selectively use the first and second curette parts 100 and 200 depending on the position of the side wall 11.

The curette tool 1000 including such a configuration allows the user to secure the nail grooming space 12 between the side wall 11 and the skin tissue by pushing out the adjacent skin tissue with the blade 120 after an insert plate 110 is inserted into the side wall 11 of the target nail 10. In this instance, Since the nail grooming space 12 is secured, the curette tool 1000 is exposed to the outside so that the whole shape of the target nail 10 can be visually confirmed. Accordingly, a user can check the target nail 10, and then, trims the nail or forms the shape of an artificial nail. Moreover, the curette tool 1000 can act as a support plate, even when the target nail 10 is partially or mostly missing, to form an artificial nail shape.

The first curette part 100 is configured to minimize skin irritation, separate cell membranes and foreign substances adhering to the side wall 11, and form the nail grooming space 12. The first curette part 100 can be selected and used according to the length and deformation degree of the side wall 11 of the target nail 10. Specifically, the first curette part 100 may include an insert plate 110 which is inserted into the target nail 10 to support the target nail, a blade 120 which after getting in contact with the surface of the nail pushes in the direction of the skin tissue adjacent to the side wall 11, and a connecting bar 130 which is formed to mount the first curette part 100 onto the grip part 300.

The insert plate 110 is a configuration that supports the toenail or fingernail by being laterally inserted into the first side wall 11a of the target nail 10. In this instance, the insert plate 110 may preferably be a long streamline-shaped plate, and may have a thickness that can be inserted between the underside of the nail and the skin. The first side wall 11a is located on one side of the target nail 10, and is placed at a position corresponding to an open direction where the blade 120 is not formed on either one side of the insert plate 110.

Specifically, the width and the size of the insert plate 110 can be selected according to the length and deformation degree of the side wall of the target nail 10. For example, the length of the insert plate 110 may be selected to correspond to the length of the side wall 11 of the target nail 10. In the case of a toenail, the side wall is preferably longer and wider than that of a fingernail. In addition, the insert plate 110 can be smoothly inserted into the side walls 11 located at both sides of the user's nail since being formed in the streamline shape, thereby separating the toenail or the fingernail from the skin without damage.

Furthermore, the insert plate 110 is formed to be relatively larger in size than the basic form to act as a support plate as the deformed shape of the target nail 10 becomes more severe. On the other hand, the insert plate 110 is formed to be relatively smaller in size than the basic form as the deformed shape of the target nail 10 is less severe, thereby preventing any risk or injury due to excessive size during use. Moreover, the insert plate 110 can act as a support plate capable of forming an artificial nail shape even when the target nail 10 is partially or mostly lost.

The blade 120 is in contact with the surface of the nail and pushes in the direction of the skin tissue adjacent to the side wall 11 to create a space, thereby separating the cell membrane and foreign materials from the surface of the nail. Such a blade 120 extends upwardly perpendicular along the outer periphery of one side of the insert plate 110, so that the insert plate 110, when inserted into the side wall 11, presses against and simultaneously supports the skin tissue. For example, in the state in which the insert plate 110 is inserted into the first side wall 11*a*, the inner end of the blade 120 is rotated in the direction of the skin tissue adjacent to the side wall 11 based on the outermost point 110*a* to push the skin tissue.

In detail, the blade 120 may include a support wing 121 formed along one side of the insert plate 110, and a guide wing 122 which is extended from the support wing 121 and protrudes from the insert plate 110. The support wing 121 is positioned on one side of the streamline-shaped insert plate 110, has a rounded outer end to prevent injury during the use of the curette tool. In addition, the support wing 121 has a specified height to safely support and push the skin tissue without irritation.

The guide wing 122 is extended from the end of the support wing 121 to be used on a normal nail and has a rounded outer end to prevent injury. Especially in a case in which the blade 120 is equipped with a guide wing 122, the insert plate 110 is reduced in size to prevent pain even when pushing the first curette part 100 into the fingernail or toenail. The guide wing 122 is supported on the surface of the nail to allow the user to use it in a stable position without shaking. Furthermore, the guide wing 122 is prepared and supported to be in contact with the surface of the target nail 10 so that the insert plate 110 can be rotated.

The blade 120 may further include an outlet 120*a* at the inner end, which is opened for a predetermined range to allow the discharge of separated cuticles or foreign materials. As described above, by forming the outlet 120*a* at the inner end of the blade 120, cuticles or foreign materials can be discharged to the outside, thereby preventing accumulation, improving usability, and allowing for the curette tool 1000 to be cleaned or wiped down without leaving water pooled or foreign materials remaining at corners.

The connecting bar 130 is configured to be extended from the inner end of the insert plate 110 to be mountable on the grip part 300. The connecting bar 130 can be made in various forms, such as a cylindrical or rectangular shape, and can be inserted and fixed in a position corresponding to the end of the grip part 300. At this time, the connecting bar 130 may have a structure that is detachable by forming a helical thread on the outer peripheral end.

The second curette part 200 is formed to be symmetrical to the first curette part 100, and can be inserted in the direction of the second side wall 11*b* of the target nail 10. That is, the first curette part 100 and the second curette part 200 are formed to be used respectively on both side walls 11 of the target nail 10, thereby allowing the user to easily use a single curette tool 1000 on the target nail 10. As described above, shape, and size of the second curette part 200 are all symmetrically formed in the same manner as the first curette part 100, and a detailed description thereof will be omitted.

The grip part 300 is made in the form of a long bar so that the user can hold it to use the curette tool 1000. In this instance, the grip part 300 is equipped so that the first and second curette parts 100 and 200 are installed at both ends thereof, thereby allowing the user to change directions according to the position of the side wall 11 of the target nail 10. Therefore, the grip part 300 can be provided with a plurality of square-shaped friction protrusions 310 formed by grooves engraved on the outer surface at predetermined intervals. As described above, the grip part 300 can prevent the user's hand from slipping during use since having the plurality of friction protrusions 310 on the outer surface on both sides, thereby providing convenience. Additionally, the grip part 300 can include connection grooves 320 corresponding to the shape of the connecting bars 130 of the first and second curette parts 100 and 200 to allow the connecting bars 130 to be inserted and mounted at the end surfaces on both sides.

According to the present invention, the first and second curette parts 100 and 200 have different types distinguished based on the shapes of the target nail 10 of the user, and may be classified into a modified expanded type 101, a modified contracted type 102, a general toenail type 103, and a general fingernail type 104. Accordingly, the first and second curette parts 100 and 200 can be selected according to the deformation degree, the usage purpose and the extent of loss of toenails and fingernails, and by selecting the optimal structure suitable for the target nail 10, it is possible to easily reconstruct the side wall 11 of the deformed nail without injuring the user.

In the case of the modified expanded type 101, the insert plate 110 is made in a streamlined shape with a set width (a) and is symmetrical on both sides, as illustrated in FIG. 1A. In the case of the modified expanded type 101, the blade 120 protrudes upward along the outer surface on one side based on the centerline of the insert plate 110. In particular, the modified expanded type 101 has the insert plate 110 which is larger in a set width (a) than the modified contracted type 102, the general toenail type 103, and the general fingernail type 104, so as to be used for nails that have undergone severe deformation or significant loss. The modified expanded type 101 can save time when trimming toenails of athlete's foot, ingrown toenails, or nails from which nail plates are separated, and can reduce the user's pain. In addition, the modified expanded type 101 is designed with the length of the insert plate 110 as long and wide as the length of the nails, thereby enhancing the effect when restoring heavily deformed nails.

The modified contracted type 102 is made in a streamlined shape with a set width (b) that is relatively narrower than the set width (a) of the modified expanded type 101, and is symmetrical on both sides as illustrated in FIG. 1B. Furthermore, the modified contracted type 102 has the blade 120 protruding upward along the outer surface on one side based on the centerline of the insert plate 110. That is, the modified contracted type 102 has a structure similar to that of the modified expanded type 101, but has a narrower width to make it suitable for use on nails with less deformation and damage only on the side wall 11.

The modified contracted type 102 is necessary for restoring nails with a slightly damaged side wall 11 using artificial nails and has a very suitable structure for nails where restoration of the side wall 11 is difficult. Therefore, the modified contracted type 102 has the width formed to support only the side wall 11, and is provided with a long and narrow-shaped insert plate 110 to minimize pain since not penetrating too deeply into the skin inside the nails.

The variable extension type 101 and the variable reduction type 102 are designed with the insert plate 110 formed in a streamlined shape extended broadly to the sides so that in cases where the nails are damaged and can no longer retain their original shape due to various causes or environments, the insert plate 110 supports the damaged or lost parts from the bottom to facilitate the shaping of artificial nails.

The general toenail type 103, as illustrated in FIG. 1C, is formed in a streamlined shape with a set width (c) for the insert plate 110, such that one side and the other side are formed symmetrically. Moreover, the general toenail type 103 has the guide wing 122 formed to be extended so that the blade 120 protrudes beyond the insert plate 110 by a predetermined length, so as to be used on normal-shaped toenails. In particular, the general toenail type 103 is formed shorter than the length of the variable reduction type 102 and can be used safely without piercing or digging into the toenail due to the outwardly protruding guide wing 122.

The general toenail type 103 is suitable for restoring slightly damaged toenails to their general form or for the sidewall 11, and can be used to extend artificial nails on normal-shaped toenails. In addition, the general toenail type 103 is very effective for slightly damaged toenails due to the skin tissue attached to the toenail.

The general fingernail type 104, as illustrated in FIG. 1D, is configured so that the insert plate 110 has a uniform width (d) in the length direction and is bent at a predetermined angle. Furthermore, the general fingernail type 104 has the guide wing 122 formed to be extended so that the blade 120 protrudes beyond the insert plate 110 by a predetermined length, so as to be used on normal-shaped toenails. In particular, the general toenail type 103 is formed shorter than the length of the variable reduction type 102 and narrower than the set width (c) of the general toenail type 103, thereby yielding a structure more suitable for hands than feet.

The general fingernail type 104 is more effective for hands than feet, and can effectively assist in extending artificial nails when fingernail breakage occurs due to fracture at stress points on the sidewall 11. Furthermore, the general fingernail type 104 can prevent side deformation of the nail to help the nail to grow into a healthy one, and is preferably used for smaller target nails 10 since being formed narrower than the variable extension type 101, variable reduction type 102, and general toenail type 103.

The general toenail type 103 and general fingernail type 104 are generally suitable for toenails and fingernails where the sidewall 11 has not collapsed, do not cause pain even when being pushed into the nail since the insert plate 110 of the first and second curette sections 100 and 200 is designed very small, and are also suitable for general toenail and fingernail care with a normally filled sidewall 11 since the blade 120 serves to separate the skin and sidewall 11 on both sides.

The curette tool 1000 according to the present invention can secure a nail grooming space by making the blade 120 contact with the surface of the nail and pushing towards the skin tissues adjacent to side wall 11, and minimize skin irritation by selecting and using suitable first and second curette parts 100 and 200 according to the length and deformation degree of the side wall 11 of a target nail, thereby enabling the separation of the cell membrane and foreign materials attached to the side wall 11 of the nail.

Furthermore, traditionally, the process of making artificial nails required the simultaneous use of two or three curettes, so only skilled professionals could use them. However, the curette tool 1000 of the present invention is easy for amateurs to use, and does not require lots of tools since only one curette tool 1000 is used, thereby significantly reducing artificial nail work time and procedure. Accordingly, the curette tool 1000 of the present invention greatly prevents the development into ingrown feet or deformed nails by using the thin first and second curette sections 100 and 200 to make artificial nails in cases where toenails or fingernails are slightly chipped by daily activities such as hitting against desks, tables, refrigerators, etc.

Figure 5:
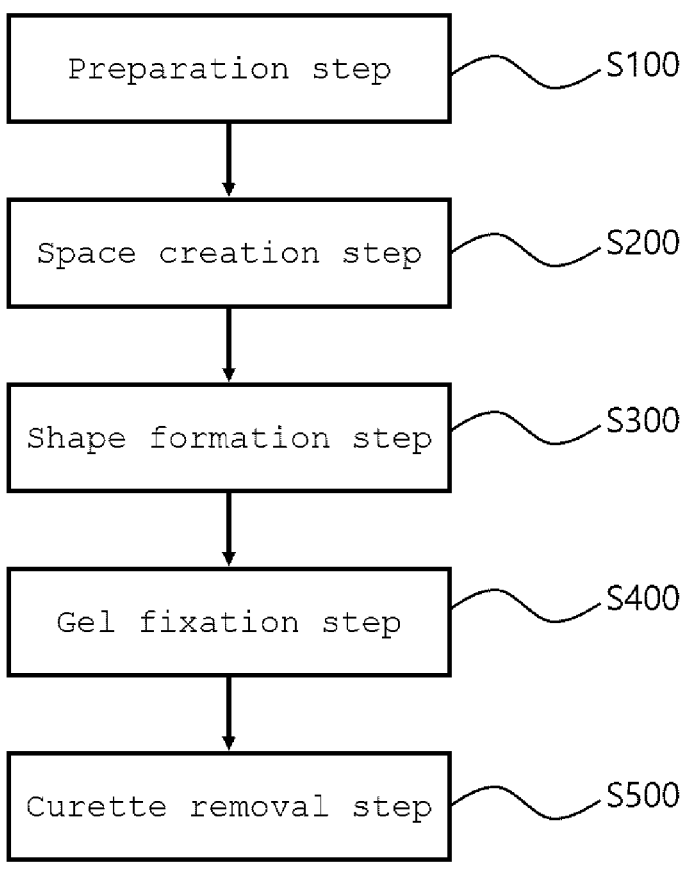
FIG. 5 is a view illustrating a sequential order of a nail care method using the curette tool according to an embodiment of the present invention.
Figure 6:
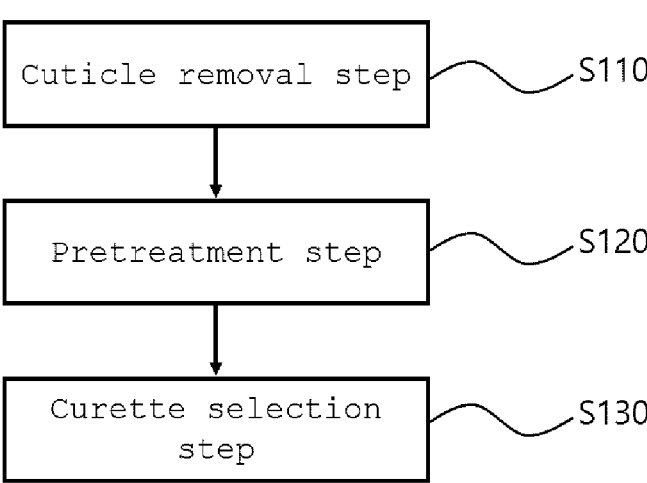
FIG. 6 is a view illustrating an accurate sequence of a preparation step of the nail care method using the curette tool according to an embodiment of the present invention.

FIG. 5 is a view illustrating a sequential order of a nail care method using the curette tool according to an embodiment of the present invention, and FIG. 6 is a view illustrating an accurate sequence of a preparation step of the nail care method using the curette tool according to an embodiment of the present invention. Referring to FIGS. 5 and 6, the nail care method using the curette tool can be performed in the order of a preparation step (S100), a space creation step (S200), a shape formation step (S300), a gel fixation step (S400), and a curette removal step (S500). The curette tool can be inserted into a side wall 11 of a target nail 10 among a user's fingernails or toenails, and then, can be rotated to secure a nail grooming space 12.

The preparation step (S100) is a step in which the curette tool 1000 to be used for the target nail 10 is prepared. The preparation step (S100) ensures that before using the curette tool 1000, the target nail 10 is groomed and first and second curette parts 100 and 200 suitable for the target nail 10 are prepared. Specifically, the preparation step (S100) can proceed in the order of a cuticle removal step (S110), a pretreatment step (S120), and a curette selection step (S130).

The cuticle removal step (S110) is a step of removing cuticles or foreign substances from the nails and trimming them. First, the thickness of the nails is measured, and is adjusted to normal thickness if it exceeds the normal thickness. At this time, the thickness can be adjusted using a nail grooming tool, and a contour line can be formed along the cuticle line. Thereafter, the cell membranes (cuticles) and foreign substances separated from the surface along the cuticle line can be wiped off and removed from the surface. Moreover, calluses or dirty areas around the nails can be cut or filed to tidy up.

The pretreatment step (S120) is a step in which each section of the target nail 10 is polished using a surface polishing tool, and then, is coated with acrylic, which is allowed to cure for a set period of time. Specifically, the target nail is divided into a round section which touches the skin surrounding the surface of the nail and has a predetermined width, a free edge section which the nail grows and protrudes from the skin, and a body section which is the central section of the nail, and can be trimmed using a file or a buffer by section. Next, acrylic can be applied to the entire surface of the nail and cured for a predetermined period of time to finish the pretreatment.

The curette selection step (S130) is a step of selecting the curette tool based on the length of the side wall 11 and the deformed shape of the target nail 10. Specifically, the curette selection step (S130) allows for the use of one of the expanded deformation type 101, the reduced deformation type 102, the general toenail type 103, or the general fingernail type 104 depending on the shape and deformation of the nail. First, it is confirmed whether the target nail 10 is a fingernail or a toenail, and then, one is selected based on the deformation degree and the presence of loss. That is, in the curette selection step (S130), first and second curette parts 100 and 200 having a relatively larger and wider structure are selected as the deformation degree and loss becomes more severe.

The space creation step (S200) is a step in which the insert plate 110 of the curette tool 1000 is inserted into the side wall 11 of the target nail 10 and the blade 120 pushes the skin tissue adjacent to the side wall 11 outward to secure a nail grooming space 12. In a state in which a user grasps the curette tool 1000 selected in the curette selection step (S130), the user inserts the insert plate 110 into the side wall 11 of the target nail 10. At this time, the blade 120 is in close contact with the skin tissue adjacent to the side wall 11, and is rotated outwards from the side wall 11 towards the skin tissue by the user's handling action. Thereafter, as the blade 120 pushes the skin tissue adjacent to the side wall 11, the nail grooming space 12 is secured between the side wall 11 and the skin tissue.

The shape formation step (S300) is a step of trimming the shape of the target nail 10 and applying gel to create an artificial nail shape. After securing the nail grooming space 12 using the curette tool 1000 in the space creation step (S200), the shape of the side wall 11 is trimmed in a state in which the side wall 11 is exposed to the outside, and then, gel is applied to the target nail 10. If a portion of the target nail 10 is missing, gel can be applied while supporting the insert plate 110 of the curette tool 1000. Next, an artificial nail shape can be formed to allow a certain length of free edge to be created on the target nail 10. The gel fixation step (S400) is a step in which the gel applied to the artificial nail shape is cured with ultraviolet light to fix it in place. In the shape formation step (S300), the gel applied to the target nail 10 is cured with ultraviolet light for a set period of time. At this time, the curette tool 1000 remains inserted in the target nail 10, thereby maintaining the fixed state without deformation of the shape of the artificial nail.

The curette removal step (S500) is a step of removing the curette tool 1000 that has been inserted into the side wall 11 of the target nail 10. After curing in the gel fixation step (S400), the curette tool 1000, which has been maintained inserted into the side wall 11 of the target nail 10, is extracted to complete the shape of the artificial nail on the target nail 10.

It will be understood by those skilled in the art that the present invention can be realized in a modified form without departing from the essential characteristics thereof. Therefore, the disclosed embodiments should be considered in a descriptive rather than a limiting sense. The scope of the invention is indicated by the claims rather than the foregoing description and all differences within the scope equivalent to the claims are to be construed as being included in the invention.

The invention claimed is:

1. A nail care method comprising:
a preparation step of preparing a curette tool, the curette tool comprising:
a first curette part which has an insert plate and a blade extending upward perpendicularly along an outer circumference on one side of the insert plate;
a second curette part which is formed symmetrically to the first curette part; and
a grip part which is formed in a bar shape with the first and second curette parts respectively installed at each end thereof,
wherein any one of the first and second curette parts is configured to be inserted into a side wall of a target nail, and the blade is configured to push a skin tissue adjacent to the side wall outwardly to secure a nail grooming space;
a space creation step in which the insert plate of the curette tool is inserted into the side wall of the target nail and the blade pushes the skin tissue adjacent to the side wall outwardly to secure a nail grooming space;
a shape formation step of trimming a shape of the target nail and applying gel to form a shape of an artificial nail;
a gel fixation step of curing and fixing the shape of the artificial nail with ultraviolet light;
a curette removal step of removing the curette tool from the side wall of the target nail.

2. The nail care method according to claim 1, wherein the preparation step comprises:
a cuticle removal step of removing cuticles or foreign substances from the target nail;
a pretreatment step of polishing a surface of the target nail by sections of the target nail by using a surface polishing tool, and then, applying acrylic and curing for a predetermined period of time;
a curette selection step of selecting the curette tool according to a length and deformed shape of the side wall of the target nail.

* * * * *